United States Patent [19]
Townsend et al.

[11] Patent Number: 5,563,055
[45] Date of Patent: Oct. 8, 1996

[54] METHOD OF AGROBACTERIUM-MEDIATED TRANSFORMATION OF CULTURED SOYBEAN CELLS

[75] Inventors: Jeffrey A. Townsend; Laurie A. Thomas, both of Des Moines, Iowa

[73] Assignee: Pioneer Hi-Bred International, Inc., Des Moines, Iowa

[21] Appl. No.: 218,852

[22] Filed: Mar. 28, 1994

Related U.S. Application Data

[63] Continuation of Ser. No. 920,409, Jul. 27, 1992, abandoned.
[51] Int. Cl.$^6$ ................................................. C12N 15/00
[52] U.S. Cl. ................... 435/172.3; 435/240.4; 435/240.45; 435/240.48; 435/240.5; 800/205; 800/DIG. 26; 935/55
[58] Field of Search ........................ 435/172.1, 172.3, 435/240.4, 240.45, 240.48, 240.49, 240.5; 935/56, 64, 67, 55; 800/205, 255, DIG. 26

[56] References Cited

U.S. PATENT DOCUMENTS 4,992,375  2/1991  Wright ................................ 435/240.5

FOREIGN PATENT DOCUMENTS

WO8912102  12/1989  WIPO .

OTHER PUBLICATIONS

W. A. Parrott et al (1989) Plant Cell Reports 7:615–617.
I. Godwin et al (1991) Plant Cell Reports 9:671–675.
M. A. W. Hinchee et al (1988) Biotechnology 6:915–922.
B. W. Delzer et al (1990) Crop Sci 30:320–322.
J. Alt–Moerbe et al. (1988) Mol Gen Genet 213:1–8.
P. Holford et al (1992) Plant Cell Reports 11:196–199.
M. S. Wright et al (1987) Plant Cell Reports 6:83–89.
H. T. Hartmann & DE Kester (1975) Plant Propagation Principles and Practices, Third Edition, Prentice Hall, pp. 291–292.
P. Guerche et al (1990) Mol. Gen. Genet. 221:306–314.
Chang, et al. (1991) *Agrobacterium tumefaciens*–mediated transformation of soybean (Glycine max (L.) Merr.) is promoted by the inclusion of potato suspension culture, *Bot. Bull. Academia Sinica*, vol. 32, pp. 171–178.
Chee, et al. (1989) Transformation of Soybean (*Glycine max*) by Infecting Germinating Seeds with *Agrobacterium tumefaciens*, *Plant Physiol.*, vol. 91, pp. 1212–1218.

Primary Examiner—Bruce R. Campbell
Attorney, Agent, or Firm—Pioneer Hi-Bred International, Inc.

[57]  ABSTRACT

A method for producing transgenic soybean plants is disclosed. The method employs conditions necessary for genotype-independent, Agrobacterium-mediated transformation of soybean explants and utilization of specialized medium to cause root induction.

10 Claims, No Drawings

METHOD OF AGROBACTERIUM-MEDIATED TRANSFORMATION OF CULTURED SOYBEAN CELLS

This is a continuation of application Ser. No. 920,809, filed Jul. 27, 1992, now abandoned.

FIELD OF THE INVENTION

The present invention relates to the production of transgenic soybean plants through Agrobacterium-mediated transformation.

BACKGROUND OF THE INVENTION

Soybean (*Glycine max*) is one of the world's most important crop plants. It is an annual seed legume grown on more than 50 million hectares for the production of oil and protein. The value of the crop is estimated to be over 20 billion dollars. Each year more than 100 million metric tons of soybean are produced. The development of gene transfer techniques for leguminous plants is of commercial interest because it facilitates the development of new cultivars with improved disease resistance, tolerance to specific herbicides and increased nutritional value. However, molecular approaches for the improvement of soybean are limited by the technology available to produce transgenic soybean plants.

Many plants, including several important crop plants, have been genetically modified using Agrobacterium-mediated gene transfer. McCormick, et al. (1986) *Plant Cell Rep.* 5, 81–84; Radke, et al. (1988) *Theor. Appl. Genet.* 75, 685–694; Umbeck, et al. (1987) *Bio/Technology* 5, 263–266; Botteman and Leemans (1988) *Trends in Genetics* 4, 219–222. Unfortunately, even though some genotypes of these dicotyledonous species are susceptible to Agrobacterium infections (Facciotti et al., (1985) *Biotechnology* 3, 241–246; Owens and Cress (1985) *Plant Physiol.* 77, 87–94; Byrne et al. (1987) *Plant Cell Tissue and Organ Culture* 8, 3–15), the use of Agrobacterium for transformation is limited due to the lack of available and efficient transformation and regeneration procedures.

Until recently soybean was considered to be outside the host range of Agrobacterium. DeCleene and DeLey (1976) *Bacterial Rev.* 42, 389–466. Later reports suggested that soybean has a limited susceptibility to Agrobacterium which is soybean genotype and Agrobacterium strain dependent. Byrne, et al. (1987) *Plant Cell Tissue Organ Cult.* 8, 3–15. Only one variety of soybean (Peking) has been successfully transformed, and further, this variety is of no commercial value. Few transgenic soybean plants of this transformable variety have been produced by cocultivation of regenerable explants with Agrobacterium. Hinchee, et al. (1988) *Bio/Technology* 6, 915–922. For transformation of soybeans via Agrobacterium-mediated methods to become commercially viable, the method must permit direct transformation of elite commercial cultivars.

In addition to these problems, soybean is known to be the most difficult Glycine species to regenerate. Explants do not readily produce roots, making further cultivations of transgenic material almost impossible. Thus, the methods used for transformation and regeneration remained unreliable and ineffective until now.

Therefore, it is an object of this invention to provide an improved method for Agrobacterium species to infect plant cells and to transfer T-DNA to the plant cells for expression therein.

It is another object of this invention to provide a novel induction medium for Agrobacterium species for enhancing the capacity of said species to infect and transform soybean plant cells.

Still another object of this invention is to provide novel growth media and methods for the regeneration of soybean explants into whole plants.

The process of this invention represents a great improvement in the techniques of Agrobacterium-mediated transformation in soybean tissue and its regeneration into transgenic soybean plants.

SUMMARY OF THE INVENTION

In accordance with this invention, there is provided a a simple, rapid, and reliable process for the production of transgenic soybean plants. The method is effective with all soybean varieties including elite commercial cultivars, and shows a substantial improvement over previously-used systems because it provides necessary and hereto-missing factors for transformation and regeneration of soybeans, and optimizes these and other factors for the successful production of healthy, fertile transgenic plants.

This invention comprises a genotype-independent method for producing a transgenic soybean plant comprising:

(a) cocultivating an explant derived from hypocotyl or cotyledonary nodes of a germinated soybean seed with Agrobacterium species containing a chimetic gene in the presence of a signal compound selected from the group consisting of acetosyringone, α-hydroxyacetosyringone, acetovanillone, syringaldehyde, syringic acid, and sinapinic acid and mixtures thereof;

(b) inducing virulence of the Agrobacterium by coculture at a temperature below 28° C.; and (c) inducing virulence of the Agrobacterium by decreasing the pH of the plant culture media below pH 6.0.

This process involves the coculture of soybean hypocotyl or cotyledonary node explants with an Agrobacterium species carrying a plasmid into which is inserted the gene or genes of interest. A soybean explant is a piece of soybean tissue that is taken from a donor plant and is capable of producing callus in culture. Soybean hypocotyl tissue is that portion of the stem of a soybean plant embryo or seedling below the cotyledons and above the root. A cotyledon is an embryonic leaf, and a cotyledonary node is that part of the seedling between the embryonic axis and the cotyledons which botanically defines the division of the hypocotyl and the epicotyl (the embryonic shoot).

Several factors which significantly impact the transformation of cultured soybean cells have been identified in arriving at this invention. The most important of these appears to be the induction of the virulence (vir) genes in Agrobacterium by proper use of signal molecules during cocultivation. Cultured soybean cells lack or have a limiting amount of the necessary signal molecules to initiate the transformation process. These results are in general agreement with other studies which have recognized the importance of vir gene induction for soybean transformation but failed to solve the problem. Delzer, et al. (1990) *Crop Sci.* 30, 320–322; Owens and Smigocki (1988) *Plant Physiol.* 88, 570–573. This invention uses acetosyringone, a phenolic compound produced by wounded plant cells, to induce the vir genes. Other phenolic compounds, α-hydroxyacetosyringone, acetovanillone, syringaldehyde, syringic acid, and sinapinic acid, also induce the vir genes and their use individually or in combination with acetosyringone can result in improved soybean transformation efficiencies. Use of adequate amounts of signal molecules in the cocultivation process has in every instance resulted in enhanced transformation frequency.

The temperature for cocultivation was discovered to be another important factor. The usual temperatures (26°–28° C.) for the culture of soybean cells are inappropriate for efficient transformation. A lower temperature resulted in highly effective transformation. The inhibition observed at 28° C. did not seem to result from overgrowth of bacteria and consequent reduction in plant cell viability at higher temperatures, because explants cocultured at both temperatures produced voluminous callus when kanamycin sulfate was excluded from the media. Media pH during coculture also affects transformation rate. Measures such as buffering at low pH (pH 5.5) ensure high efficiency. While not intending to be limited by theory, it is believed these improved efficiencies are related to signal molecule response operation. It is known that vir gene induction is temperature and pH dependent with an optimum at approximately 20° C. and pH 5.5. Alt-Moerbe, et al. (1988) *Mol. Gen. Genet.* 213, 1–8.

The successful transformation of soybean cells was also dependent upon the concentration of bacteria in the inoculum. In general, higher numbers of bacteria resulted in more transformation events. Although a saturating concentration of bacteria may exist, above which no additional transformation events are produced, for soybean cells, this number appears to be very high. Our experiments suggest that the number may be approached by a single 30 minute inoculation with bacteria at or exceeding $3\times10^8$ viable cells/ml, and that conventional concentrations of $3\times10^7$ cells/ml (Deblaere, et al. (1987) *Meth. Enzymology* 153, 277–293.) are far too low.

However, in our work, a truly saturating condition for inoculation could not be identified. The sequential inoculations demonstrated that transformable soybean cells were not being targeted even when inoculations were conducted with very high concentrations of bacteria. One problem encountered when attempting to inoculate with high concentrations of bacteria was the tendency for aggregation of the bacterial cells. Aggregation resulted in a reduction in the number of bacteria available for attachment to plant cells. Aggregation began immediately upon resuspension of sedimented bacteria, and the rate of aggregation was concentration dependent. It was also dependent on the degree of mechanical mixing of the media. The composition of the cocultivation media (in which the bacteria are resuspended) can also influence aggregation. Therefore, only complete plant cell media appropriate for the induction of rapid division of plant cells and high level induction of the Agrobacterium vir genes were used in this process.

Substantial increases in transformation frequency were achieved using inoculation conditions which limited the aggregation phenomenon and accounted for its effects. First, inoculations were conducted with high initial bacteria concentrations at room temperature with a minimum of mixing. Second, they were conducted in batches such that each explant was inoculated with a newly resuspended pellet of Agrobacterium in log growth phase. The wounding of the explant was done in the inoculum, in the presence of the highest possible concentration of available bacteria (i.e. before aggregation significantly reduced the number of independent cells).

Third, the period of inoculation was no less than thirty minutes, beginning when the last explant in a given batch had been wounded. Longer time periods did not result in enhanced transformation frequency. Sequential inoculation resulted in a modest increase in frequency. The increase was probably due to an increase in the number of bacteria available to transform the plant cells. From these experiments, it is clear that soybean cells can tolerate long periods of exposure to high concentrations of Agrobacterium.

By using conditions which assure vir gene induction and providing the necessary high concentration of Agrobacterium, we have for the first time been able to achieve consistently high frequencies of soybean transformation. The method of this invention produces these frequencies with several different strains of Agrobacterium and is only marginally affected by the original susceptibilities of soybean varieties to Agrobacterium infection.

After transformation, explants are cultivated in liquid counterselection medium, then transferred to solidified selection medium, and the process is repeated as described in the art for identification by transgenic markers such as gus. McCabe, et al. (1988) *Bio/Technology* 6, 922–926. Shoots are induced in transgenic explants by known methods. Wright, et al. (1986) *Plant Cell Reports* 5, 150–154; Barwale, et al. (1986) Planta 167, 473–481. The shoots are excised and, by the addition of pyroglutamic acid to a hormone-enriched growth medium, roots are readily induced. This is contrary to reports that roots are rarely induced from soybean tissue and then only in hormone-free medium. Whole mature, reproductive plants are produced after transfer to greenhouse culture in soil.

DETAILED DESCRIPTION OF THE INVENTION

We have expressed the β-glucuronidase (gus) gene from *Escherichia coli* in soybean hypocotyl cells after cocultivation with *Agrobacterium tumefaciens* carrying the gus gene. Disarmed strains of Agrobacterium harboring binary plasmids with chimeric gus and neomycin phosphotransferase II (npt II) genes were vectors for DNA transfer. After cocultivation, soybean hypocotyl explants from the commercial cultivars listed in Table 1 were cultured on callus induction medium (Hinchee, et al. (1988) *Bio/Technology* 6, 915–922) containing 100 μg/ml kanamycin sulfate. Transformation events were scored three weeks after cocultivation when hypocotyl explants were assayed histochemically for gus activity. Transformation events were visualized with the aid of a dissecting microscope (10× magnification). They appeared as sectors of stained plant cells. Stable integration of the gus gene into the soybean chromosome was suggested by the retention of gene activity in the sibling cell population within the stained sectors. Multiple, independent events could be detected on some explants. These were bounded on all sides by cells not expressing the gus gene. Sets of explants were inoculated, cocultured, selected and histochemically assayed together. Each set was an independent experimental unit, the numbers of explants being sufficient to compensate for variation due to genetic difference (within a seed lot), explant orientation (within a seedling) and explant size. Treatments were scored by recording the total number of events detected on the explants in them. Using this method only transformed cells capable of sustained division were scored. The measurements were clearly distinguished over background gus activity and any residual bacterial contamination.

Signal molecules.

Table 1 shows the results of an experiment in which hypocotyl explants of eight different soybean varieties were inoculated (30 minutes) and cocultured (3 days) in the presence and in the absence of acetosyringone (100 μM). Inoculum was prepared by resuspending log phase Agrobacterium in liquid plant cell media buffered with 10 mM MES to pH 5.5 with or without acetosyringone at a final concentration of $3 \times 10^8$ viable cells/ml. Explants were prepared in the inoculum, held there for 30 minutes and then transferred to agar solidified media for the 3 day cocultivation. Cocultivation was conducted at 22° C. After cocultivation, the explants were washed and transferred to solid media containing antibiotics (kanamycin) for selection of transformed plant cells and counterselection of Agrobacteria. Subsequent culture was at 28° C. Transformed sectors were produced only when acetosyringone was added to the inoculation and cocultivation media. Transformed sectors were produced on all of the varieties. The average number of transformed sectors produced on each variety (48 explants) was 107. The number of transformed sectors ranged from a low of 44 (variety Carter) to a high of 153 (variety 9391). In subsequent experiments, a few transformed sectors were produced on explants which did not see acetosyringone but the frequency of such events was too low to be accurately measured.

Inclusion of acetosyringone in the overnight bacterial culture and in a bacterial preculture period with plant media resulted in no enhancement of transformation frequency. Similar results were obtained when the monosaccharide glucose was incorporated in the inoculation and cocultivation media (data not shown). All subsequent experiments were conducted with acetosyringone included in the inoculation and cocultivation media at 100 μM.

TABLE 1

Number of transformed sectors produced by cocultivation of soybean hypocotyl explants with and without acetosyringone.

| Soybean genotype | Acetosyringone (μM) | |
|---|---|---|
| | 0 | 100 |
| Peking | 0 | 147 |
| Williams 82 | 0 | 115 |
| Cartter | 0 | 44 |
| 9273 | 0 | 79 |
| 9302 | 0 | 117 |
| 9341 | 0 | 115 |
| 9391 | 0 | 153 |
| 9582 | 0 | 87 |
| Mean | — | 107 |

Temperature.

Table 2 shows the results of an experiment in which hypocotyl explants which had been inoculated in a common petri dish were divided randomly into two sets. The sets (24 explants each) were cocultivated on solid media at different temperatures, 22° C. and 28° C. for three days. After cocultivation all explants were cultured at 28° C. Twelve separate inoculations were conducted using variety 9341 with Agrobacterium at $3 \times 10^8$ viable cells/ml for thirty minutes. The mean number of transformed sectors produced on 24 explants cocultured at 22° C. was 109. The mean number of 28° C. transformed sectors was 1.4. In this experiment there is a roughly 80 fold increase in transformation frequency resulting from cocultivations at reduced temperature. All subsequent cocultivations were conducted at 22° C.

TABLE 2

Number of transformed sectors produced by cocultivation of soybean hypocotyl explants at 22 and 28 degrees Celsius.

| | Temperature (°C.) | |
|---|---|---|
| Inoculation | 22 | 28 |
| 1 | 101 | 1 |
| 2 | 109 | 2 |
| 3 | 134 | 0 |
| 4 | 97 | 2 |
| 5 | 127 | 1 |
| 6 | 102 | 1 |
| 7 | 100 | 1 |
| 8 | 84 | 1 |
| 9 | 112 | 4 |
| 10 | 118 | 3 |
| 11 | 100 | 0 |
| 12 | 124 | 1 |
| Mean | 109 | 1.4 | pH.

Table 3 gives the results of an experiment in which explants were inoculated and cocultured at different pH levels; 5.5, 5.75 and 6.0. Fourteen separate inoculations were made at each pH. Media was buffered with 10 μm MES to insure pH stability. Coculture then proceeded on similarly buffered, solidified media for three days. The mean number of transformed sectors produced on 24 explants at pH 6.0 was significantly lower (203) than that produced at either pH 5.5 (286), or pH 5.75 (288). This is contrary to published results showing no demonstrated effect of pH on *Glycine max* when using acetosyringone. Godwin, et al. (1991) *Plant Cell Rep.* 9, 671–675. All subsequent inoculations and cocultivations were conducted with media adjusted to pH 5.5 and buffered with 10 μM MES.

TABLE 3

Number of transformed sectors produced by cocultivation of soybean hypocotyl explants at pH 5.50, 5.75 and 6.00.

| | pH | | |
|---|---|---|---|
| Inoculation | 5.50 | 5.75 | 6.00 |
| 1 | 186 | 324 | 210 |
| 2 | 278 | 307 | 192 |
| 3 | 301 | 263 | 162 |
| 4 | 473 | 334 | 312 |
| 5 | 192 | 232 | 92 |
| 6 | 245 | 256 | 129 |
| 7 | 264 | 288 | 186 |
| 8 | 206 | 312 | 105 |
| 9 | 253 | 313 | 245 |
| 10 | 259 | 249 | 239 |
| 11 | 270 | 263 | 241 |
| 12 | 484 | 344 | 309 |
| 13 | 315 | 260 | 203 |
| 14 | 283 | 287 | 212 |
| Mean | 286 | 288 | 203 |

Concentration of viable bacteria in the inoculum.

Table 4 shows the results of two experiments where explants (variety were inoculated with different concentrations of bacteria. For these experiments log phase overnight bacterial cultures were sedimented and then resuspended by serial dilution to the appropriate concentration. In each experiment three separate dilution series of bacteria were prepared from a common overnight culture. As in the previous experiments 48 explants were prepared in each inoculum, held there for 30 minutes and then cocultured on solid media for three days. The total number of transformed sectors produced for each inoculation of 48 explants was recorded. For the first three inoculation concentrations: $3 \times 10^7$, $10^8$ and $3 \times 10^8$ cells/ml more transformed sectors were produced by more bacteria. This was true for both experiments and for every dilution series.

TABLE 4

Number of transformed sectors produced by inoculation of soybean hypocotyl explants with different concentrations of Agrobacterium

| Experiment/ Dilution Series | $3 \times 10^7$ | $10^8$ | $3 \times 10^8$ | $10^9$ |
|---|---|---|---|---|
| 1/A | 31 | 96 | 187 | 179 |
| 1/B | 92 | 176 | 254 | 253 |
| 1/C | 67 | 156 | 183 | 228 |
| 2/A | 220 | 349 | 409 | 414 |
| 2/B | 232 | 448 | 493 | 503 |
| 2/C | 224 | 386 | 464 | 464 |
| Mean | 144 | 269 | 332 | 340 |

At a higher inoculation concentration, $10^9$ cells/ml, no increase in transformation frequency was detected. The mean number of sectors produced at this concentration did not differ significantly from that of the concentration below it. The dose/response profile thus changes at $3 \times 10^8$ cell/ml from one where bacteria are limiting to one where they are saturating.

The absolute number of transformants produced at a given concentration varies substantially between experiments. Since a plateau is apparently reached in each experiment the condition of the Agrobacteria, rather than the numbers of them, is likely to be the limiting factor. It is also possible that the different soybean explant preparations varied in their capacity for transformation. A third possibility is that the real length of the inoculations varied between experiments. Though this was unlikely, experiments were conducted to define an inoculation time period sufficient to saturate a given concentration. A period of thirty minutes was determined to produce maximal numbers of events with additional time having no effect (data not shown).

Sequential inoculation.

In an attempt to force the Agrobacteria to infect the soybean cells, an experiment was conducted wherein sets of 48 soybean hypocotyl explants (variety 9341) were inoculated once or twice for 30 minutes each with bacteria at $5 \times 10^8$ viable cells/ml. All explants were cocultured for three days. The results are shown in Table 5. The average number of transformed sectors was significantly higher (315) for the 2× treatment than it was for the 1× treatment (286). It appears that additional transformation events may be produced by sequential inoculation. It is believed that true saturation of the pool of transformable soybean cells is not accomplished by a single inoculation and numbers of viable bacteria remain limiting even when inoculations are made at very high concentrations. However, the great majority of associations which lead to transformation occur in the first thirty minute inoculation.

TABLE 5

Effect of sequential inoculation on Agrobacterium mediated transformation of soybean hypocotyl.

| | 1X | 2X |
|---|---|---|
| | 275 | 281 |
| | 325 | 386 |

TABLE 5-continued

Effect of sequential inoculation on Agrobacterium mediated transformation of soybean hypocotyl.

| | 1X | 2X |
|---|---|---|
| | 271 | 251 |
| | 274 | 341 |
| Mean | 286 | 315 |

Susceptible and resistant soybean genotypes.

The results presented in Table 1 showed that all soybean varieties tested can be transformed by Agrobacterium using the method of this invention. To determine the relative susceptibility of soybean varieties to Agrobacterium-mediated transformation matched pair analyses of putative resistant varieties, Corsoy 79 and Century were conducted with variety Peking as the sensitive partner. Inoculations were conducted in petri dishes with stainless steel mesh dividers (0.5 mm pore) so that explants of the different varieties could be prepared in a common inoculum. Twenty-four explants of the 'resistant' varieties were prepared in each of twelve separate petri dishes containing an equal number of 'sensitive' explants. The results are given in Table 6. Variety Peking was transformed at approximately two times the frequency of variety Century and approximately three times the frequency of variety Corsoy 79. While variety dependent susceptibility is confirmed by these experiments the degree, 2–3 fold, is small enough as to have no serious implications regarding the use of Agrobacterium in transformation of diverse soybean germplasm.

TABLE 6

Comparison of susceptibility of selected soybean genotypes to Agrobacterium-mediated transformation.

| | Peking | Century | Peking | Corsoy 79 |
|---|---|---|---|---|
| 1 | 101 | 46 | 76 | 48 |
| 2 | 49 | 49 | 81 | 58 |
| 3 | 105 | 42 | 99 | 34 |
| 4 | 29 | 4 | 143 | 41 |
| 5 | 43 | 1 | 131 | 25 |
| 6 | 27 | 7 | 85 | 51 |
| 7 | 13 | 22 | 144 | 17 |
| 8 | 34 | 13 | 84 | 20 |
| 9 | 31 | 9 | 192 | 31 |
| 10 | 39 | 16 | 124 | 38 |
| 11 | 19 | 13 | 0 | 0 |
| 12 | 3 | 1 | 3 | 1 |
| Mean | 41 | 19 | 97 | 30 |

Agrobacterium strain.

Two alternate, disarmed Agrobacterium strains were compared with the octopine strain, LBA4404 for their ability to mediate transformation of soybean hypocotyl cells; they were the L,L-succinamopine strain EHA 101 and the nopaline strain C58-pz707. Table 7 shows the results of an experiment in which increasing concentrations of each of these strains are used to inoculate Williams 82 hypocotyl explants. Forty-eight explants were inoculated with each concentration of each strain. LBA4404 was included as a control at $3 \times 10^8$ viable cells/ml. Both of the strains produced transformed sectors. In both cases the transformation frequency was dependent upon the concentration of bacteria in the inocula, with more bacteria producing more transformation events. At the levels tested neither gave a substantial change in transformation as compared with LBA4404.

TABLE 7

Comparison of transformation of soybean hypocotyl by selected strains of *Agrobacterium tumefaciens*.

| Strain | Viable cells/ml | | | | |
| --- | --- | --- | --- | --- | --- |
| | $10^7$ | $3 \times 10^7$ | $10^8$ | $3 \times 10^8$ | $10^9$ |
| LBA4404 | — | — | — | 258 | — |
| EHA101 | 16 | 38 | 51 | 155 | 274 |
| C58-pZ707 | 11 | 13 | 118 | 262 | — |

The following examples illustrate various applications in accordance with the invention, but are in no way intended to limit the scope thereof.

EXAMPLE 1

Soybean (*Glycine max*) seed, Pioneer variety 9341, was surface sterilized by exposure to chlorine gas evolved in a glass bell jar. Gas was produced by adding 3.5 ml hydrochloric acid (34–37% w/w) to 100 ml sodium hypochlorite (5.25% w/w). Exposure was for 16–20 hours in a container approximately one cubic foot in volume. Surface sterilized seed was stored in petri dishes at room temperature. Seed was germinated by plating on ¹/₁₀ strength agar solidified medium according to Gamborg [B5 basal medium with minimal organics, Sigma Chemical Co., cat. no. G5893, 0.32 gm/L; sucrose, 0.2% w/v and 2-[N-morpholino]ethanesulfonic acid (MES), 3.0 mM] without plant growth regulators and culturing at 28° C. with a 16 hour day length and cool white fluorescent illumination of approximately 20 $\mu Em2S1$. After three or four days, seed could be prepared for cocultivation. The seed coat was removed and the elongating radicle was removed 3–4 mm below the cotyledons. Ten prepared seed were held in each of several petri dishes.

EXAMPLE 2

Overnight cultures of *Agrobacterium tumefaciens* strain LBA 4404 harboring the binary plasmid p12GUSBN17 (DP1816) or p12-4X (DP1813), grown to log phase in Minimal A medium containing tetracycline, 1.0 µg/ml, were pooled and an optical density measurement at 550 nm was taken. Sufficient volume of the culture was placed in 15 ml conical centrifuge tubes such that upon sedimentation between 1.0 and $2.0 \times 10^{10}$ cells were collected in each tube, where O.D.550 $1.0 = 1.4 \times 10^9$ cells/ml. Sedimentation was by centrifugation at 6000 g for 10 minutes. After centrifugation the supernatant was decanted and the tubes were held at room temperature until inoculum was needed but not longer than one hour.

EXAMPLE 3

Inoculations were conducted in batches such that each plate of seed was treated with a newly resuspended pellet of Agrobacterium. One at a time the pellets were resuspended in 20 ml inoculation medium. Inoculation medium consisted of B5 salts (G5893), 3.2 gm/L; sucrose, 2.0% w/v. 6-benzylaminopurine (BAP), 44 µM; indolebutyric acid (IBA), 0.5 µM; acetosyringone (AS), 100 µM and was buffered to pH 5.5 with MES, 10 mM. Resuspension was by vortexing. The inoculum was then poured into a petri dish containing prepared seed and the cotyledonary nodes were macerated with a surgical blade. This was accomplished by dividing seed in half by longitudinal section through the shoot apex preserving the two whole cotyledons. The two halves of the shoot apex were then broken off their respective cotyledons by prying them away with a surgical blade. The cotyledonary node was then macerated with the surgical blade by repeated scoring along the axis of symmetry. Care was taken not to cut entirely through the explant to the abaxial side. Twenty explants were prepared in roughly five minutes and then incubated for 30 minutes at room temperature without agitation. Additional plates were prepared during this time. After 30 minutes the explants were transferred to plates of the same medium solidified with Gelrite (Merck & Co., Inc.), 0.2% w/v. explants were embedded with the adaxial side up and level with the surface of the medium and cultured at 22° C. for three days under cool white fluorescent light, approximately 20 $\mu Em^2S^1$.

EXAMPLE 4

After three days the explants were moved to liquid counterselection medium. Counterselection medium consisted of B5 salts (G5893), 3.2 gm/L; sucrose, 2.0% w/v; BAP, 5.0 µM; IBA, 0.5 µM; vancomycin, 200 µg/ml; cefotaxime, 500 µg/ml and was buffered to pH 5.7 with MES, 3 mM. Ten explants were washed in each petri dish with constant, slow gyratory agitation at room temperature for four days. Counterselection medium was replaced four times.

EXAMPLE 5

The explants were then picked to agarose solidified selection medium. Selection medium consisted of B5 salts (G5893), 3.2 gm/L; sucrose, 2.0%, w/v; BAP, 5.0 µM; IBA, 0.5 µM; kanamycin sulfate, 50 µg/ml; vancomycin, 100 µg/ml; cefotaxime, 30 µg/ml; timentin, 30 µg/ml and was buffered to pH 5.7 with MES, 3.0 mM. Selection medium was solidified with SeaKem agarose, 0.3% w/v. The explants were embedded in the medium, adaxial side down and cultured at 28° C. with a 16 hour day length and cool white fluorescent illumination of 60–80 $\mu Em^2S^1$.

EXAMPLE 6

After two weeks explants were again washed with liquid medium on the gyrotory shaker. This time the wash was conducted overnight in counterselection medium containing kanamycin sulfate, 50 µg/ml. The following day explants were picked to agarose solidified selection medium. Again they were embedded in the medium, adaxial side down, Culture was as before for another two week period.

EXAMPLE 7

After one month on selective media transformed tissue became visible as green sectors of regenerating tissue against a background of bleached, less healthy tissue. Explants without green sectors were discarded, explants with green sectors were transferred to elongation medium. Elongation medium consisted of B5 salts (G5893), 3.2 gm/L; sucrose, 2.0% w/v; IBA, 3.3 µM; gibberellic acid, 1.7 µM; vancomycin, 100 µg/ml; cefotaxine, 30 µg/ml; and timentin, 30 µg/ml, buffered to pH 5.7 with MES, 3.0 mM. Elongation medium was solidified with gelrite, 0.2% w/v. They were embedded adaxial side up and cultured as before. Culture was continued on this medium with transfers to fresh plates every two weeks. When shoots became 0.5 cm in length they were excised at the base and placed in rooting medium in 13×100 mm test tubes. Rooting medium consisted of B5 salts (G5893), 3.2 gm/L; sucrose, 15 gm/L; nicotinic acid, 20 µM; pyroglutamic acid (PGA), 900 mg/L and IBA, 10 µM. It was buffered to pH 5.7 with MES, 3.0 mM and solidified with Gelrite, 0.2% w/v. After ten days the shoots were transferred to the same medium without IBA or PGA. Shoots were rooted and held in these tubes under the same environmental conditions as before.

EXAMPLE 8

When a root system was well established the plantlet was transferred to sterile soil mix in plant cons (ICN Biomedicals, Inc., cat. no. 26-720 & 1-02). Temperature, photoperiod and light intensity remained the same as before, Under these conditions the regenerants became vigorous, mostly normal (though small) plants. When their root systems again became well established a corner of the plant con was cut off and the plants were gradually hardened off in an environmental chamber or greenhouse. Finally they were potted in soil mix and grown to maturity, bearing seed, in a greenhouse.

We claim:

1. A method for transforming soybean cells, comprising the steps of
    (A) providing a complete plant medium that supports rapid division of plant cells, said medium comprising
        (i) a virulence-inducing amount of a signal molecule,
        (ii) a growth promoting amount of an auxin, and
        (iii) *Agrobacterium tumefaciens* bacteria in log growth phase, such that said bacteria are present in said medium in a concentration of about $10^8$ viable cells per ml,
    wherein said bacteria contain a chimeric gene and said medium is buffered at a pH below 6.0;
    (B) introducing into a first portion of said medium a plurality of germinated soybean seeds, from each of which seeds seed coat and radicle have been removed, and separating the cotyledons of each seed so as to expose the cotyledonary node of each seed, whereby a plurality of explants is produced; then
    (C) macerating said cotyledonary node, without cutting entirely through each of said explants to the abaxial side thereof, and thereafter maintaining said explants in said first portion, at room temperature, for at least about 30 minutes; then
    (D) transferring said explants to a second portion of said medium in solidified form, such that said explants are embedded in said medium, adaxial side up and level with the surface of said medium, and culturing said explants for about 3 days at about 22° C.;
    (E) treating said explants in counterselection medium;
    (F) cultivating said explants in agarose-solidified selection medium, wherein said explants are embedded adaxial side down in said selection medium, whereby transformed cells in said explants are favored; and then
    (G) selecting transformed cells from said explants.

2. A method according to claim 1, wherein said signal molecule is at least one selected from the group consisting of acetosyringone, α-hydroxyacetosyringone, acetovanillone, syringaldehyde, syringic acid and sinapinic acid.

3. A method according to claim 1, wherein step (C) further comprises replacing said first portion with fresh medium at least once, whereby sequential inoculation of said explants is effected.

4. A method according to claim 1, wherein said concentration in step (A)(iii) is between $10^8$ and $10^9$ viable cells per ml.

5. A method according to claim 1, wherein said maintaining of said explants in said first portion is effected with a minimum of mixing of the medium.

6. A method according to claim 1, wherein said auxin is indolebutyric acid.

7. A method according to claim 1, wherein said chimeric gene encodes a seed storage protein.

8. A method according to claim 7, wherein said chimeric gene encodes *Bertholletia excelsa* 2S storage protein.

9. A method according to claim 1, further comprising after step (G) the steps of inducing a shoot in said explants, excising said shoot from said explant, and then inducing said shoot to establish a root system by exposing said shoot to rooting medium that contains an effective amount of pyroglutamic acid and indolebutyric acid.

10. A method according to claim 9, further comprising the step of transferring said shoot to soil such that said root system is secured within said soil to nourish said shoot, allowing it to develop into a plant.

* * * * *